(12) United States Patent
Sahraie

(10) Patent No.: US 8,702,233 B2
(45) Date of Patent: Apr. 22, 2014

(54) VISION EXERCISING APPARATUS

(75) Inventor: Arash Sahraie, Aberdeenshire (GB)

(73) Assignee: NovaVision, Inc., Boca Raton, FL (US)

( * ) Notice: Subject to any disclaimer, the term of this patent is extended or adjusted under 35 U.S.C. 154(b) by 821 days.

(21) Appl. No.: 11/993,357

(22) PCT Filed: Jun. 30, 2006

(86) PCT No.: PCT/GB2006/002422
§ 371 (c)(1),
(2), (4) Date: Apr. 17, 2008

(87) PCT Pub. No.: WO2007/003902
PCT Pub. Date: Jan. 11, 2007

(65) Prior Publication Data
US 2010/0141894 A1   Jun. 10, 2010

(30) Foreign Application Priority Data
Jun. 30, 2005  (GB) .................................. 0513603.1

(51) Int. Cl.
*A61B 3/00*   (2006.01)
*A61B 13/00*  (2006.01)

(52) U.S. Cl.
USPC ........................................ 351/203; 600/558

(58) Field of Classification Search
USPC ......... 351/203–205, 200, 208, 209, 239, 224, 351/246; 398/18, 51; 600/356, 383, 600/400–402, 404–406, 558
See application file for complete search history.

(56) References Cited

U.S. PATENT DOCUMENTS

| | | | |
|---|---|---|---|
| 4,822,162 A * | 4/1989 | Richardson et al. | .......... 351/243 |
| 4,971,434 A | 11/1990 | Ball | |
| 4,995,717 A | 2/1991 | Damato | |
| 5,534,953 A * | 7/1996 | Schmielau | .................... 351/203 |

(Continued)

FOREIGN PATENT DOCUMENTS

| | | |
|---|---|---|
| DE | 9305147 | 8/1994 |
| WO | WO2007/0109724 | 9/2007 |
| WO | WO2008/013907 | 1/2008 |

OTHER PUBLICATIONS

The Shorter Oxford English Dictionary on Historical Principles, C.T. Onions (Ed.), 3rd Edition, vol. II, p. 1343, Clarendon Press, Oxford.

(Continued)

*Primary Examiner* — Thomas K Pham
*Assistant Examiner* — Brandi Thomas
(74) *Attorney, Agent, or Firm* — RatnerPrestia

(57) ABSTRACT

A vision exercising apparatus including a visual display device (1); a locating means (5) for locating the head of a user at a position to provide a substantially known relationship between the visual display device (1) and the field of view of the user; display position control means for actuating the visual display device (1) to display a predetermined pattern at a known display position which corresponds to a specific viewing area of the field of view of the user; user actuable response means (17) to enable a user response to be provided; further control means to control the display position control means to repeatedly display the predetermined pattern at the known display condition; and means to collate user response and to evaluate the statistical significance of the user response for that display position. A predetermined pattern can thus be displayed in the field of view of a user that requires exercising.

26 Claims, 12 Drawing Sheets

(56) References Cited

U.S. PATENT DOCUMENTS

| | | | |
|---|---|---|---|
| 5,539,482 | A | 7/1996 | James et al. |
| 5,565,949 | A | 10/1996 | Kasha |
| 5,883,692 | A | 3/1999 | Agonis |
| 5,912,723 | A | 6/1999 | Maddess |
| 6,068,377 | A * | 5/2000 | McKinnon et al. ............ 351/221 |
| 6,364,486 | B1 | 4/2002 | Ball et al. |
| 6,464,356 | B1 | 10/2002 | Sabel et al. |
| 6,540,355 | B1 * | 4/2003 | Couture ........................ 351/203 |
| 6,662,036 | B2 * | 12/2003 | Cosman ........................ 600/411 |
| 6,876,758 | B1 | 4/2005 | Polat et al. |
| 7,549,743 | B2 | 6/2009 | Huxlin et al. |
| 7,594,728 | B2 * | 9/2009 | Seal et al. .................... 351/210 |
| 2003/0163060 | A1 * | 8/2003 | Maddess et al. ............. 600/544 |
| 2003/0193646 | A1 * | 10/2003 | Liberman .................... 351/203 |
| 2005/0094099 | A1 * | 5/2005 | Newman et al. ............. 351/205 |
| 2005/0151152 | A1 * | 7/2005 | Miller et al. ................. 257/103 |
| 2005/0213033 | A1 | 9/2005 | Sabel |

OTHER PUBLICATIONS

Huxlin K.R., et al., Training-Induced Recovery of Visual Motion Perception after Extrastriate Cortical Damage in the Adult Cat, Cerebral Cortex, Jan. 2004, vol. 81, pp. 81-90.

U.S. Appl. No. 60/641,589, filed 1-6-200N by Applicant Huxlin et al.
U.S. Appl. No. 60/647,619, filed Jan. 26, 2005 by Applicant Huxlin et al.
U.S. Appl. No. 60/665,909, filed Mar. 28, 2005 by Applicant Huxlin et al.
Ball, Katherine K.; Beard, Bettina L.; Roenker, Daniel L.; Miller, Richard L.; and Griggs, David S., Age and Visual Serach: Expanding the Useful Field of View, Journal of the Optical Society of America, 1988, A 5, pp. 2210-2219.
International Preliminary Report and Written Opinion of PCT/US2007-064520 (WO/2007/109724), Beate Giffo-Schmidt, Authorized Officer of the International Bureau of WIPO, Sep. 23, 2008.
Examiner's First Report on Patent Application No. AU 2007226838, Australia Patent Office, Mar. 15, 2012.
Examination of Canadian Patent No. 2,613,223; CIPO, issued, Apr. 5, 2013.
International Search Report of PCT/US2007/016840 (WO2008/013907), Timen Schut, Authorized Officer of The International Bureau of WIPO, Mar. 28, 2008.
International Preliminary Report and Written Opinion of PCT/US2007/016840 (WO2008/013907), Timen Schut, Authorized Officer of The International Bureau of WIPO, Jan. 27, 2009.
Examiner's First Report on Patent Application No. AU 2007277139, Australia Patent Office, Apr. 26, 2012.

* cited by examiner

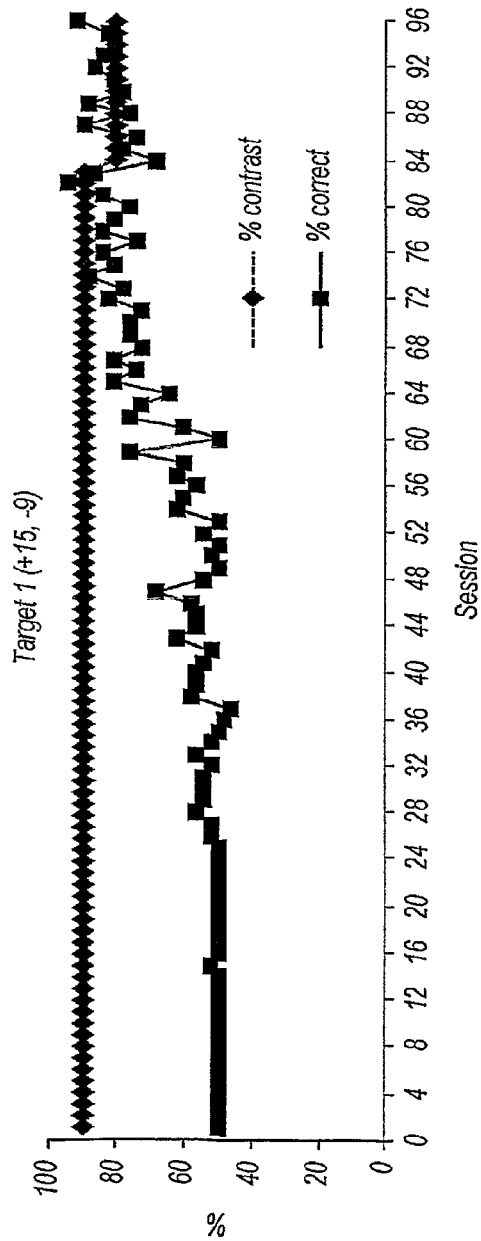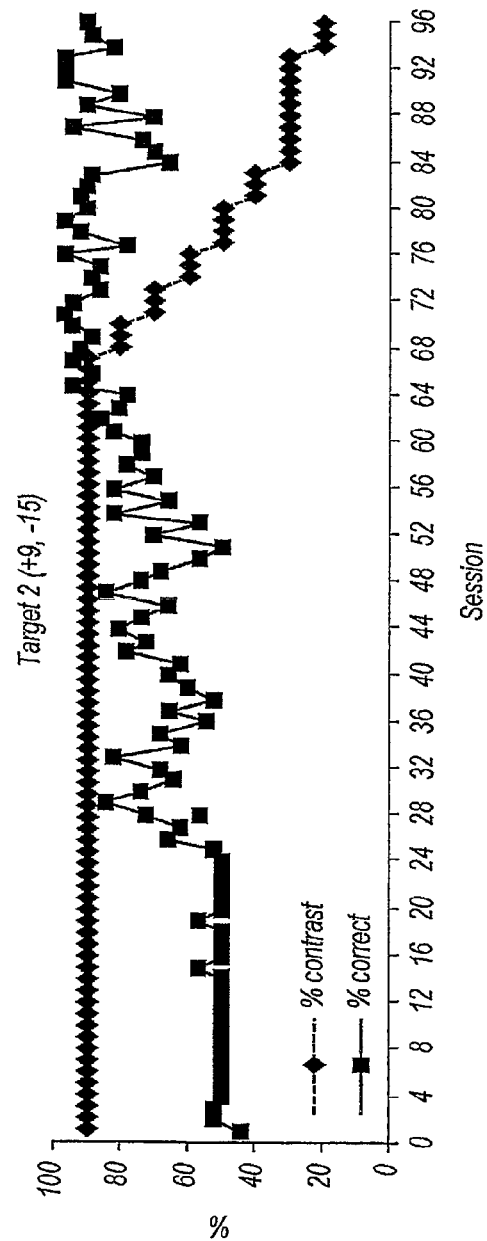

VISION EXERCISING APPARATUS

FIELD OF THE INVENTION

The present invention relates to a vision exercising apparatus.

DESCRIPTION OF THE PRIOR ART

Cortical blindness is caused by loss of or damage to the section of the cerebral cortex responsible for vision, known as the visual cortex, through a stroke or traumatic brain damage.

Unlike other forms of visual impairment, the condition is not caused by any deficiency in the eyes themselves. Further, in many cases, damage to the visual cortex only affects one brain hemisphere and therefore does not cause total blindness. Instead, sufferers of cortical blindness may have a visual field defect, known as a "blindfield", in their field of view, with otherwise normal vision. That said, within this visual field defect some specific residual visual capacities may still be demonstrated. These abilities have been termed "blind sight". In this connection, stimulus attributes such as orientation, colour, motion, illusory contours, emotional expressions and limited semantic processing have been reported within the visual field defects in some cases.

Following an incident causing loss or damage to the visual cortex, there is typically a period of limited recovery within the first few months (termed "spontaneous recovery") after which the size and location of visual field defect stabilises. It is often assumed that following this period, the remaining visual field defect is permanent and stable. However, there is some evidence that repeated stimulation within the borders of the visual field defect over extended periods of time may lead to improvements in sensitivity of the visual field defect at its borders. For example, in some tests, after repeated practice patients have shown improvements in detecting a small light target at the borders of the visual field defect. However, a problem with this type of testing is that these measurements are sensitive to small gaze shifts which may compromise the accuracy of the visual field results. In any event, it has been postulated that these improvements in sensitivity result from the stimulation of surviving neurons at the boundary of the visual field defect. Accordingly, such vision stimulating exercises must be precisely adapted to the requirements of a particular user so as to specifically target the boundary region of their visual field defect. As such, these have required the close supervision of a medical practitioner. This is clearly impractical in many cases, especially since the exercises are only effective if carried out regularly, preferably daily.

SUMMARY OF THE INVENTION

It is an object of the present invention to overcome or at least alleviate these problems.

According to one aspect of the present invention there is provided a vision exercising apparatus comprising:—
a visual display device;
locating means for locating the head of a user at a position to provide a substantially known relationship between the visual display device and the field of view of the user;
display position control means for actuating the visual display device to display a predetermined pattern at a known display position, the display position corresponding to a specific viewing area of the field of view of the user whilst located in the locating means;

user actuable response means actuable by the user to enable a user response to be provided when the user considers the predetermined pattern has been viewed during use of the apparatus;
further control means to control the display position control means to repeatedly display the predetermined pattern at the known display position; and
means to collate, for the present user, user response to display of the predetermined pattern at the known display position and to evaluate the statistical significance of the user response for that display position.

Due to the alignment of the locating means and the visual display device, it is straightforward for the predetermined pattern to be displayed at a position corresponding with a viewing area in the field of view of the user that requires exercising, for example the blind-field of a user with cortical blindness. The repeated display of the predetermined pattern at the predetermined display position exercises the user's vision in that viewing area. Over time, this exercise results in an improvement in the user's ability to detect the predetermined pattern. Further, by employing a pattern and stimulating a user's vision over a specific viewing area, it is possible to improve sensitivity even deep within a user's visual field defect. Moreover, by collating the user response to display of the predetermined pattern, the apparatus is able to provide an indication of how successful the user is at detecting the predetermined pattern at a given display position, so that their improvement over time can be monitored.

The further control means preferably controls the display position control means to display at a particular display position according to the current user.

In this way, the apparatus can accommodate different users who require different areas of their field of view to be exercised, so that time need not be spent exercising an area of their field of view where it is not required.

The further control means preferably controls the display position control means to display the predetermined pattern at a known display position a particular number of times during a single usage of the apparatus.

The number of times the predetermined pattern is displayed at a known display position should be chosen to achieve a balance between factors such as the optimum duration of the exercise and the reliability of the evaluation of the user response.

The further control means preferably controls the display position control means to display the predetermined pattern at a particular number of known display positions during a single usage of the apparatus.

In this way, different areas in the field of view of the user can be exercised.

The further control means preferably controls the display position control means to display the predetermined pattern at a maximum contrast for a new user of the apparatus.

The higher the contrast of the predetermined pattern, the easier it is to detect. The apparatus is thus set at its easiest level for a new user of the apparatus.

The further control means preferably controls the display position control means to reduce the contrast of the predetermined pattern when the statistical significance of the user response is greater than a predetermined level and increases the contrast of the predetermined pattern when the statistical significance of the user response is less than a predetermined level.

In this way, the apparatus is configured to make the exercise progressively harder as the user's ability to detect the predetermined pattern improves, thereby facilitating further improvement.

The further control means preferably controls the display position control means to reduce the contrast of the predetermined pattern by a greater amount than the amount by which the display control means increases the contrast.

Alternatively, the further control means may control the display position control means to reduce the contrast of the predetermined pattern by an amount equal to the amount by which the display control means increases the contrast.

In a preferred embodiment, the apparatus further comprises means for providing the user with an indication of when display of the predetermined pattern could take place.

The means for providing the user with an indication of when display of the predetermined pattern could take place conveniently comprises an audible signal and means for presenting said audio signal to the user in predetermined timing relationship to the display.

The user is thus made aware of when they can expect the predetermined pattern to be displayed.

Preferably, the predetermined pattern is in the form of a grating comprising a plurality of cycles of alternating dark and light linear features.

Alternatively, predetermined patterns in the form of dots and/or checks may be used.

For grating patterns, the number of cycles of alternating dark and light linear features is preferably substantially in the range 0.01 to 10.0 per angular degree of the field of view.

More preferably, the number of cycles of alternating dark and light linear features is substantially in the range 0.5 to 7.0 per angular degree of the field of view.

Experimental data has shown that grating patterns having a spatial frequency within this range are better detected by users than grating patterns having a spatial frequency outside this range.

More preferably still, the number of cycles of alternating dark and light linear features is substantially 1.0 per angular degree within the field of view.

The predetermined pattern may conveniently be contained within a substantially circular boundary.

Alternatively, the predetermined pattern may be contained within a substantially square boundary.

Preferably, the diameter or side of the boundary subtends an angle substantially in the range from 1 to 30 degrees in the field of view of the user.

More preferably, the diameter or side of the boundary subtends an angle substantially in the range from 2 to 12 degrees in the field of view of the user.

More preferably still, the diameter or side of the boundary subtends an angle of substantially 6 degrees in the field of view of the user.

Such dimensions allow for evaluation of the effect based on currently acceptable measurements of the field defect by Humphrey's Visual Field Analyser program 30-2.

The predetermined patterns may be static or dynamic.

Preferably, the further control means controls the display position control means to display the predetermined pattern at a temporal frequency substantially in the range of 1 to 30 Hz.

This allows for improved detection of the predetermined pattern by users, because visual stimuli which change over time activate the blind-field better than static stimuli.

More preferably, the further control means controls the display position control means to display the predetermined pattern at a frequency of substantially 10 Hz.

The temporal frequency may be achieved by flashing or counterphasing the predetermined pattern, or by drifting the predetermined pattern across the display screen.

Alternatively, the predetermined pattern may be rotated on the display screen.

In preferred embodiments, the apparatus further includes attraction means to attract the gaze of the user to a preselected position to assist in providing the substantially known relationship between the visual display device and the field of view of the user.

This attraction means operates to steady the gaze of the user in an appropriate direction for detecting the display of the predetermined pattern.

The user actuable response means may conveniently comprise a tactile electronic device whose condition can be changed by touch or motion in response to the observer's perception of said stimulus.

Alternatively, the user actuable response means may be voice operated.

The visual display device may conveniently comprise a computer screen or projector.

The locating means may conveniently comprise an adjustable chin rest.

In preferred embodiments, the apparatus further comprises memory means for storing one or more user profiles and wherein deficient areas in the user field of view are stored in the memory means;

wherein the further control means selects the known display position according to the profile and stores in the memory means the user response to display of the predetermined pattern at the known display position.

In this case, the further control means may select the known display position to correspond to a viewing area of the field of view of the user where the user has restricted or no vision.

According to another aspect of the present invention there is provided a computer readable medium containing program code for configuring a computer and visual display device as a vision exercising apparatus together with a locating means which locates the head of a user at a position to provide a substantially known relationship between the visual display device and the field of view of the user, the computer readable medium comprising:— first program code for actuating the visual display device to display a predetermined pattern at a known display position, the display position corresponding to a specific viewing area of the field of view of the user whilst located in the locating means;

second program code for determining a user response when the user considers the predetermined pattern has been viewed during use of the apparatus;

third program code for controlling the display position control means to repeatedly display the predetermined pattern at the known display position; and fourth program code for collating the user response to display of the predetermined pattern at the known display position and for evaluating the statistical significance of the user response for that display position.

BRIEF DESCRIPTION OF THE DRAWINGS

An example of the present invention will now be described with reference to the accompanying drawings in which:—

FIGS. 7a, 7b and 7c, are graphs showing an example set of user response data.

DETAILED DESCRIPTION OF EXEMPLARY EMBODIMENTS

Figure 1:
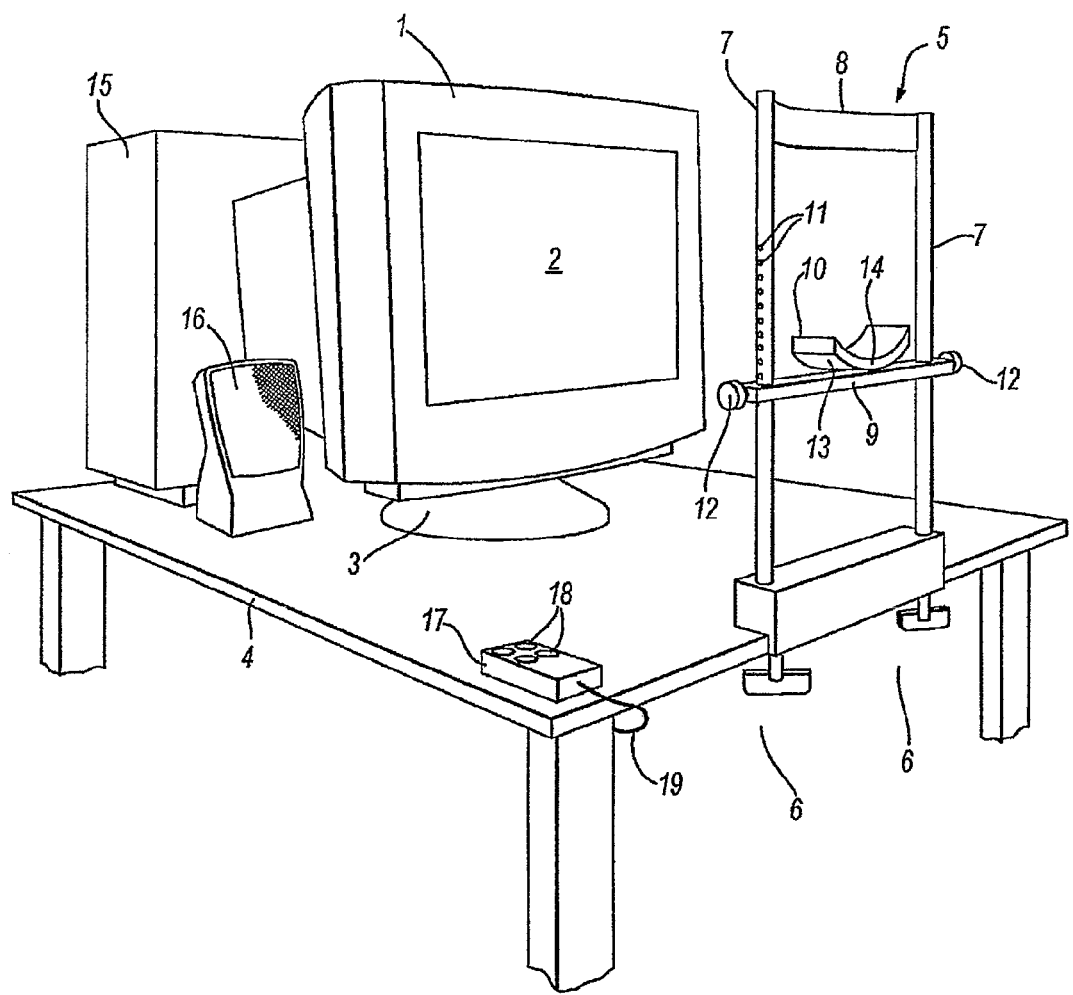
FIG. 1 shows a vision exercising device embodying the present invention.

FIG. 1 shows a vision exercising device embodying the present invention. A monitor (1) which has a screen (2) is mounted on a stand (3) and located on a platform (4) which supports the monitor at a suitable height. In the present embodiment a Cathode Ray Tube (CRT) monitor is used. However, alternative visual display devices would be equally suitable, for example, a flat panel LCD or plasma screen, or a forward/rear projection system. The weight of the monitor means that it will not readily move with respect to the platform. However, the stand may be attached to the platform, for example by means of screws, to ensure that the monitor cannot move with respect to the platform. Further, the angle of the monitor with respect to the stand may be fixed in order to prevent variation in the screen position.

A head locating means (5) for locating the head of a user with respect to the screen (2) is clamped to the platform (4) at a predetermined position by a pair of clamps (6). The head locating means comprises a pair of poles (7) which extend vertically upwards from the platform to a height approximately level with the top of the monitor (1). The poles are separated by a width which is sufficient for a user's head to fit comfortably therebetween.

A forehead rest (8) is formed from a rectangular metal or plastic strip which extends substantially horizontally between the poles (7) at the top thereof, and curves towards the screen (2) between the poles to accommodate the forehead of a user facing the screen.

The form and location of the forehead rest are determined such that when a user's forehead is located against the strip, their field of view is approximately positioned in a substantially known relationship with the screen (2).

A bar (9), which supports a chin rest (10), extends substantially horizontally between the poles (7) below the forehead rest (8). The bar (9) is slidably engaged with the poles by means of cylindrical holes formed towards each end of the bar, through which the poles pass, such that the height of the bar, and thus the chin rest (10), is adjustable. A pair of screws which engage with corresponding notches (11) in the poles are provided for fixing the bar in position at various heights. The screws, which are turned by means of knobs (12), are inserted in screw holes which extend through the bar in its longitudinal direction to connect the cylindrical holes to the adjacent ends of the bar. By turning the knobs, the screws are caused to project into or be retracted from the cylindrical holes to engage or disengage with the notches. When the screws are retracted from the cylindrical holes, the bar (9)'is free to slide up and down the poles (7) such that the bar can be aligned with notches (11) on the poles at an appropriate height for a particular user. The knobs (12) can then be turned to cause the screws to project into the cylindrical holes where they engage with the notches to hold the bar in position.

The chin rest (10) is located centrally on the bar (9), and comprises a metal or plastic strip (13), which curves upwards at either end. The strip is lined with one or more layers of a foamed material (14) for comfort.

The height of the chin rest (10) may thus be adjusted depending on the size of the user's head, such that their head is comfortably supported from below while their forehead is located against the forehead rest (8).

By adjusting the height of the chin rest, the user's field of view can be more precisely positioned in the substantially known relationship with the screen (2).

Other forms of head locating means will be straightforward for the person skilled in the art to implement. For example, in the present embodiment, the chin rest is adjustable, while the forehead rest is fixed. However, the chin rest may be fixed, and the forehead rest adjustable, or both rests may be adjustable.

A chair (not shown) is provided for the user to sit on when using the apparatus. The height of the chair should be adjustable for different users, who are thus able to sit comfortably while their head is maintained in the required position by the head locating means.

A Central Processing Unit (CPU) is provided in a housing (15) and connected to the monitor (1) either remotely or via a cable. Computer program code stored in the CPU, causes the CPU to act as a control means for displaying visual stimuli on the screen (2), and for collecting and collating a user's response thereto.

When activated, the CPU repeatedly displays a visual stimulus having a predetermined pattern at one or more known display positions on the screen (2). As discussed above, when the user's head is located by the head locating means (5), the field of view of the user is positioned in a substantially known relationship with the screen. Thus, the known display positions correspond to substantially known viewing areas of the field of view of the user.

A speaker (16) is connected to the CPU by a cable (not shown). The CPU causes the speaker to present an audio signal to the user at predetermined times coordinated with the repeated display of the visual stimulus, in order to indicate to the user the time intervals during which they may expect to view the stimulus.

A user actuable response means in the form of a response box (17) which comprises a plurality of buttons (18) is also connected to the CPU by a cable (19). The user indicates when they consider the visual stimulus has been viewed by pressing one or more of the buttons (18). When the user presses one of the buttons, a signal is transmitted via the cable (19) to the CPU, which stores the response data in a database on a memory means such as a magnetic disk.

Although, in the present embodiment, the user actuable response means is a response box comprising a plurality of buttons, other response means may additionally or alternatively be used, for example, a PC mouse, a touch sensitive screen, or a speech encoder.

With this system, the user's vision in one or more preselected areas of their field of view is exercised by the repeated display in the appropriate location or locations on the screen (2) of the visual stimulus. Over time, this exercise results in an improvement in the user's ability to detect the visual stimuli. The CPU is configured to monitor this improvement by collating the response data for each user and evaluating the statistical significance of the user's response for each display position in order to determine how successful the user is at detecting the visual stimulus at that position. The CPU is further configured to adjust the contrast of the visual stimulus for each display position to make the stimulus easier or more difficult to detect, this adjustment being based on the user's previous level of success for that position. The contrast of the stimulus is the ratio of the difference in intensity between the lightest and the darkest areas of the pattern to the sum of these intensities. In the present embodiment, new users of the apparatus start with this contrast set to maximum. Alternatively, a lower contrast setting appropriate for a particular user may be set by an operator. If they can reliably detect the stimulus at maximum contrast, over a pre-defined number of consecutive sessions, then the contrast is lowered for their next session using the apparatus. If, as a result, the performance on the lower contrast is poor, the contrast is increased. On the other hand, if the performance gradually improves and becomes reliably better, then the contrast is lowered further. In this way, the system is able to determine an optimum level of difficulty for a particular user, and to make the stimuli progressively more difficult to detect as the user's performance improves, in order to promote further improvement.

Figures 2A, 2B:
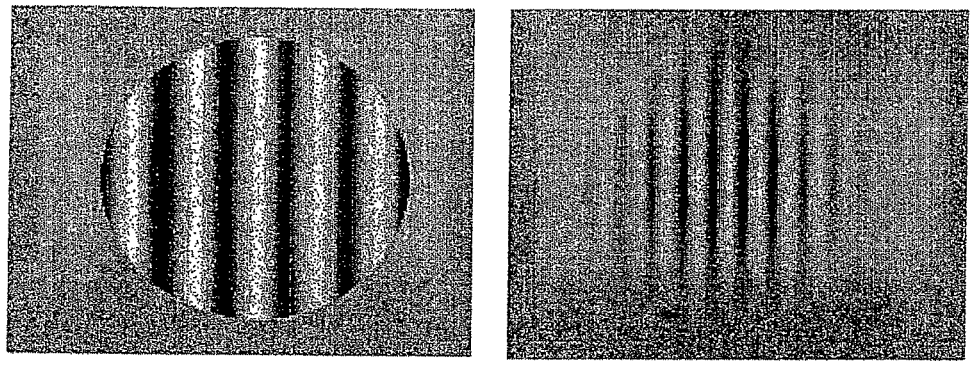
FIGS. 2a and 2b show alternative examples of suitable grating patterns for use as the predetermined pattern of a visual stimulus.

The most effective pattern for the visual stimulus has been found to be a grating pattern, although patterns of dots or checks etc. may also be used. Examples of suitable grating patterns are shown in FIGS. 2a and 2b. The grating patterns of FIGS. 2a and 2b are contained within a substantially circular boundary, although the patterns may equally be contained within a substantially square or rectangular boundary, or a boundary of any other geometric shape.

The boundary may be sharply defined, as in FIG. 2a, or may be smoothed, as in FIG. 2b.

The grating patterns may be generated optically (i.e., with an optical set-up including slides or projection systems) in a manner which would be straightforward for the person skilled in the art to implement. Alternatively, the grating patterns may be generated graphically on a computer, for example, based on the mapping of screen pixels.

Figure 3:
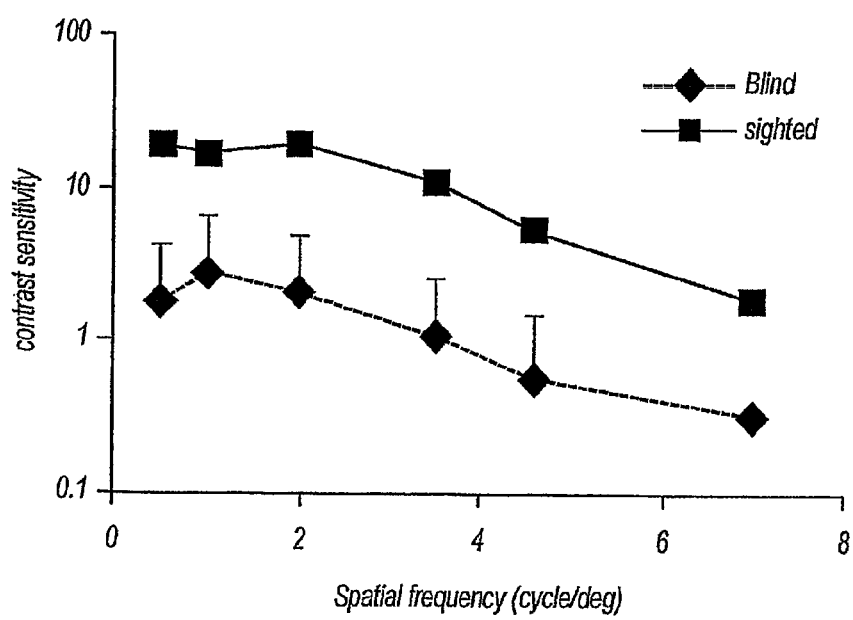
FIG. 3 is a graph of spatial frequency of a grating pattern against contrast sensitivity in the sighted and blind-field of view of a subject with cortical blindness.
Figure 4:
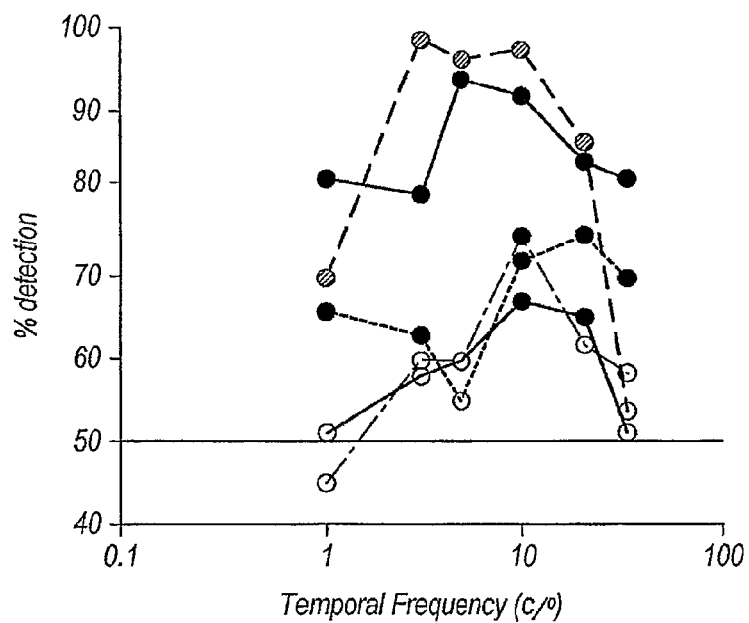
FIG. 4 is a graph of temporal frequency of a flashing visual stimulus against percentage detection for a number of subjects.

Experimental data on the measurement of contrast sensitivity in the blindfield has shown that grating patterns having a spatial frequency (i.e., number of cycles of alternating dark and light linear features per degree of visual angle) in the range of 0.5 to 7.0 cycles per degree are detected by users better than other frequencies. Best results are achieved at around 1.0 cycles per degree, as may be seen from FIG. 3. Further, stimuli that change over time (dynamic stimuli) have been shown to activate the blind-field better than static stimuli. Flashing stimuli are thus preferred. The flash-rate (temporal frequency) should preferably be in the range of 1 to 30 Hz, with optimum results being obtained at 5 to 20 Hz, as may be seen from FIG. 4. Similarly, a temporal frequency may be achieved by counterphasing, i.e., dark areas change to light, and light areas change to dark.

Alternatively, for visual stimuli with predetermined patterns such as grating patterns, which have a substantially uniform spatial frequency, a temporal frequency can be achieved by drifting the predetermined pattern in an appropriate direction, and at a certain speed, across the display screen. For grating patterns formed of light and dark line elements, the appropriate direction would be perpendicular to the orientation of these line elements. The temporal frequency in Hertz is then given by the spatial frequency in cycles per degree, multiplied by the drift speed in degrees per second.

Visual stimuli which change with time may also be achieved by rotating the predetermined pattern on the display screen.

Figure 5:
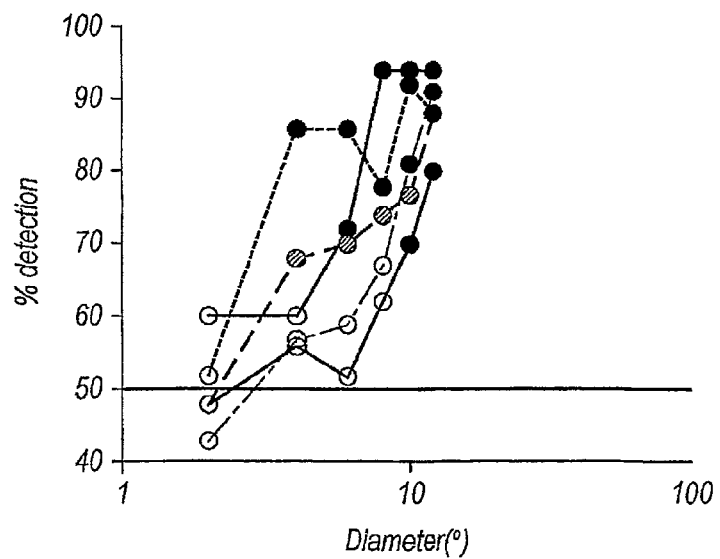
FIG. 5 is a graph of the angle subtended by the diameter of the boundary of the predetermined pattern against percentage detection for a number of subjects.

The diameter (for patterns contained within a circular boundary), or side (for patterns contained within a square boundary), of the boundary of the pattern preferably subtends an angle substantially in the range from 2 to 12 degrees in the field of view of the user, with the best results being obtained for a diameter (or side) subtending approximately 6 degrees in the field of view of the user, as may be seen from FIG. 5. This diameter allows for evaluation of the effect based on currently acceptable measurements of the field defect by Humphrey's Visual Field Analyser program 30-2.

The operation of an embodiment of the present invention is described in more detail below, with reference to the flowcharts of FIGS. 6a, 6b and 6c.

Figure 6A:
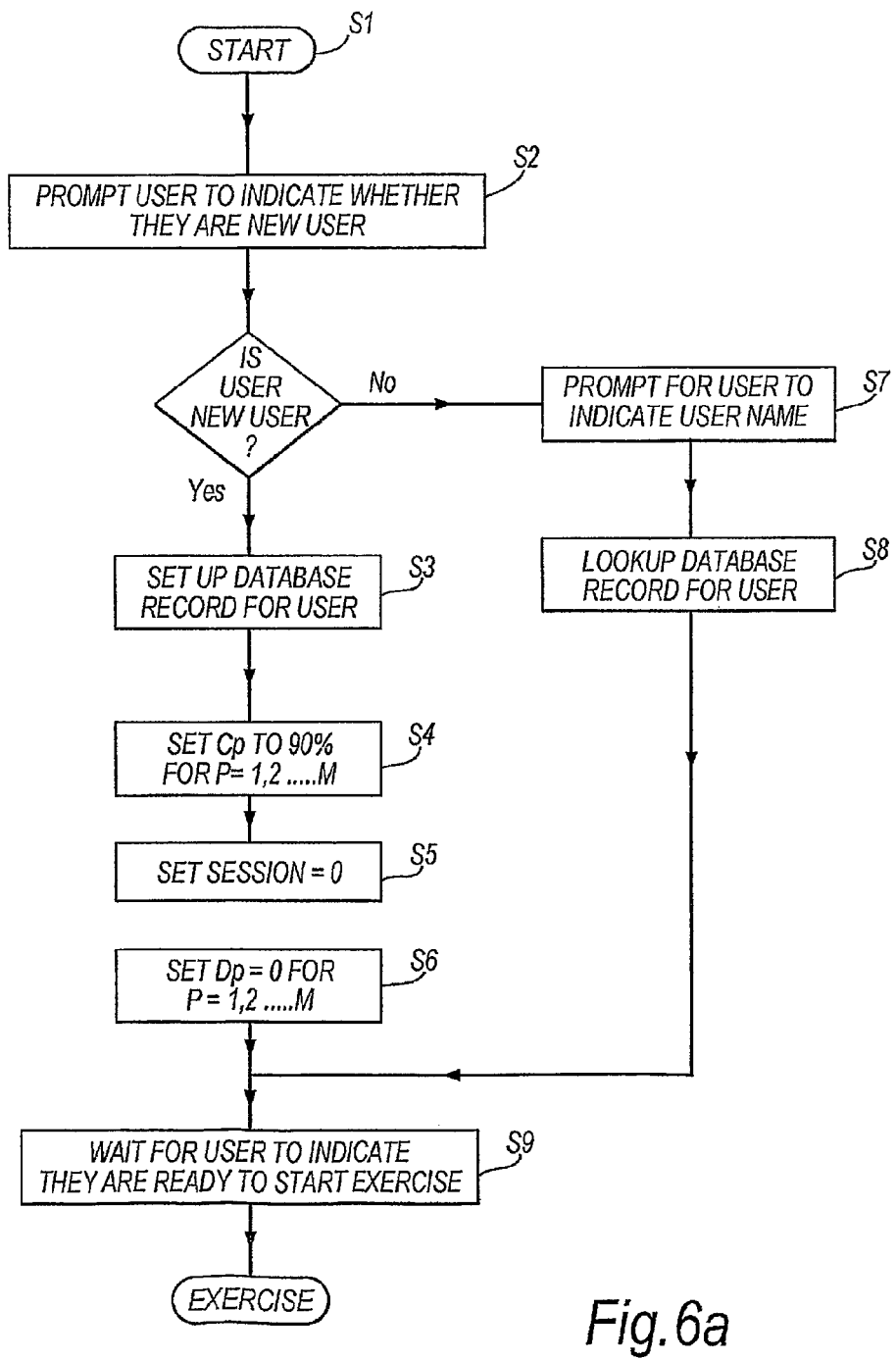
FIGS. 6a, 6b and 6c are flow charts illustrating the operation of an embodiment of the present invention.

With reference to FIG. 6a, initially (S1), the CPU is switched on, the program code is initiated, and a user is seated facing the screen (2), with their head located in the head locating means (5), to achieve a substantially known relationship between the screen (2) and the field of view of the user, as described above.

In this state, the user is requested to indicate whether they are a new user (i.e. whether they have previously set up a database record using the system), either by prompting on the screen, by audio signals through the speaker (18), or by an operator (S2).

If it is determined that they are a new user, the system proceeds to S3, where a database record is set up for the user. The database record includes a set of variables $C_P$, (where P=(1, 2, ... M), M being the total number of display positions) which determine the contrast setting for the visual stimuli in the different display positions P. These variables are each set for maximum contrast (90% for the present embodiment) (S4). Thus, a new user of the system is initially presented with the easiest to detect visual stimuli in each of the display positions. A variable SESSION representing the number of the session is set to 0 (S5), and a set of variables $D_P$, where P=(1, 2, ... M), is set to 0 (S6), indicating that the number of consecutive sessions for which the user can be considered to have successfully detected the visual stimulus is currently zero. The system then waits for the user to indicate that they are ready to start the exercise (S9).

If, at S2, the user is determined to be an existing user, the system proceeds to S7, where it waits for the user to input identifying information such as a user name via the buttons (18) on the response means. Once the user has identified themselves, the system looks up the database record for that user (S8). As for a new user, the database record includes a set of variables $C_P$ which determine the contrast setting of the visual stimuli in the different display positions. These variables have been set in accordance with the user's previous performance, as described in more detail below. The system then waits for the user to indicate that they are ready to start the exercise (S9).

The exercise starts when the user indicates that they are ready by pressing one of the buttons (18). At this point the system proceeds to the routine "EXERCISE" illustrated by the flowchart of FIG. 6*b*.

Figure 6B:
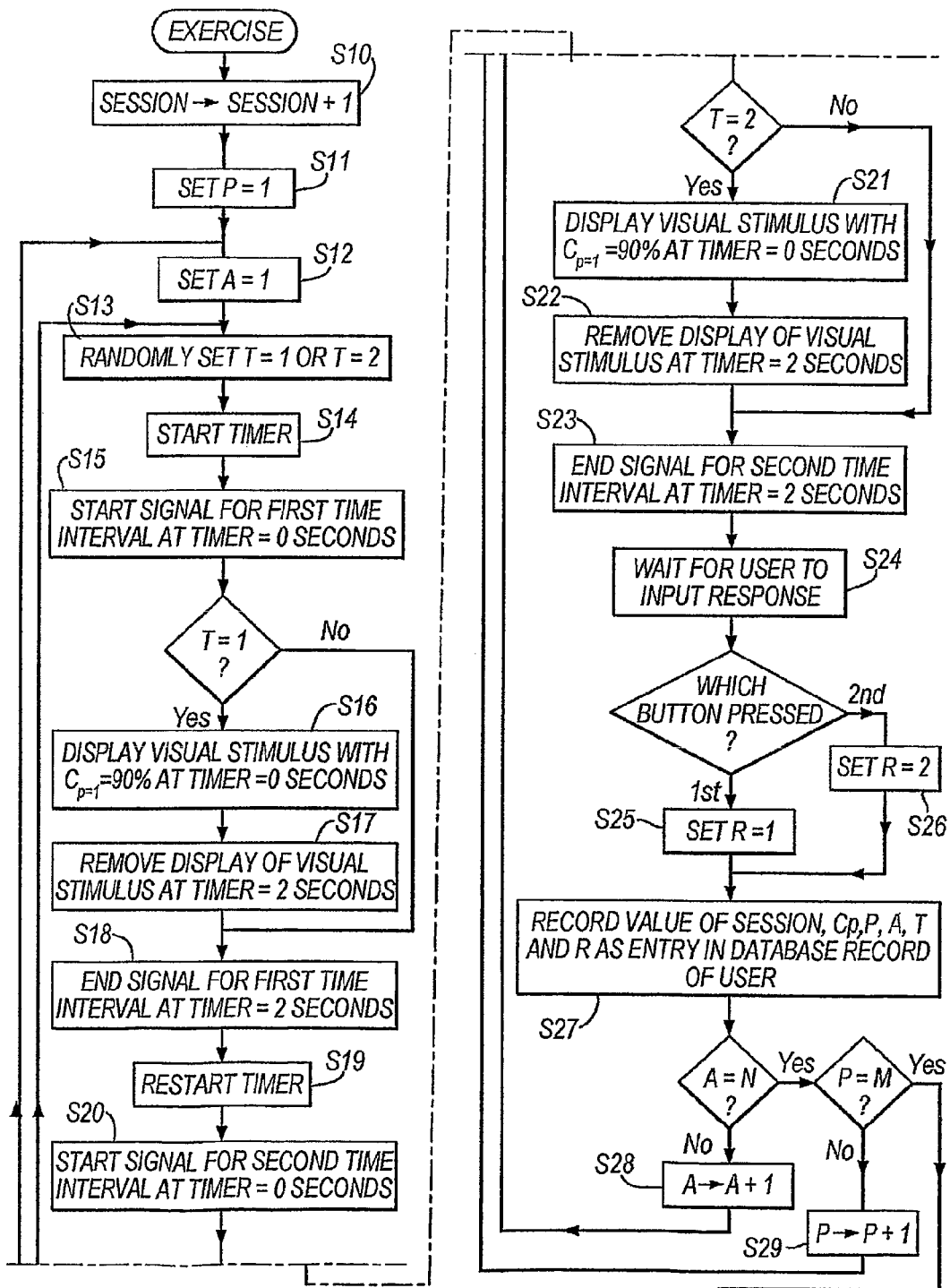

With reference to FIG. 6*b*, initially, the variable SESSION is incremented by 1 (S10). Then, a variable P, representing the display position is set to 1 (S11), and a counter A is set to 1 (S12). While P=1, the visual stimuli are presented at a first of the different display positions, and the contrast for the display position is determined by the variable $C_{P=1}$, which is stored in the user's database record.

During the exercise, the user is repeatedly presented with two consecutive time intervals, identified by audio signals sounded at the beginning and end thereof. In the present embodiment, these time intervals each have a duration of approximately 2 seconds. For each repeat, the visual stimulus is displayed during only one of the two time intervals. To this end, before the start of the first of the two time intervals, the system randomly allocates either the value 1 or the value 2 to a variable T (S13). A timer then starts to time the first time interval (S14), and an audio signal indicating the start of the first time interval is simultaneously sounded (S15). If T=1, then the visual stimulus is displayed for the duration of the first time interval (S16, S17), whereas, if T=2, the visual stimulus is not displayed. At the end of the first time interval, an audio signal indicting the end of the first time interval is sounded (S18). Subsequently, the timer is reset (S19) and starts to time the second time interval, and a signal indicating the start of the second time interval is simultaneously sounded (S20). If T=2, then the visual stimulus is displayed for the duration of the second time interval (S21, S22), whereas, if T=1, the visual stimulus is not displayed. At the end of the second time interval, an audio signal indicting the end of the second time interval is sounded (S23). Clearly, since T must either take the value 1 or 2, the visual stimulus is always displayed in one or other of the time intervals, and never both.

At the end of the second time interval, the system waits for the user to indicate during which time interval they believe the visual stimulus was displayed (S24). The user achieves this by pressing a first one of the buttons (18) if they believe that the visual stimulus was displayed during the first time interval, or a second one of the buttons (18) if they believe that the visual stimulus was displayed during the second time interval. If the first button is pressed, a variable R takes the value 1 (S25), while if the second button is pressed, the variable R takes the value 2 (S26). The value of the variable R is then recorded as a database entry together with the values of the variables SESSION, $C_P$, T and P, and the counter A (S27). After the user has indicated their response in this way, A is incremented by 1 (S28), the system returns to S13, and the process is repeated.

After each repeat, before A is incremented by 1 at S28, it is determined whether the process has been repeated a certain number of times (A=N), and the system proceeds to S29 once it is determined that A=N. At S29, P is incremented by 1, so that P takes a value corresponding to the next display position. The system then returns to S12, where, the counter A is reset to 1 so that the process is repeated N times for the next display position. Each time it is determined that A=N, the system determines whether the exercise has been performed for all the display positions, i.e., whether P=M, in which case the routine "EXERCISE" terminates, and the system proceeds to the routine "ANALYSIS", which is illustrated by the flowchart of FIG. 6*c*.

Figure 6C:
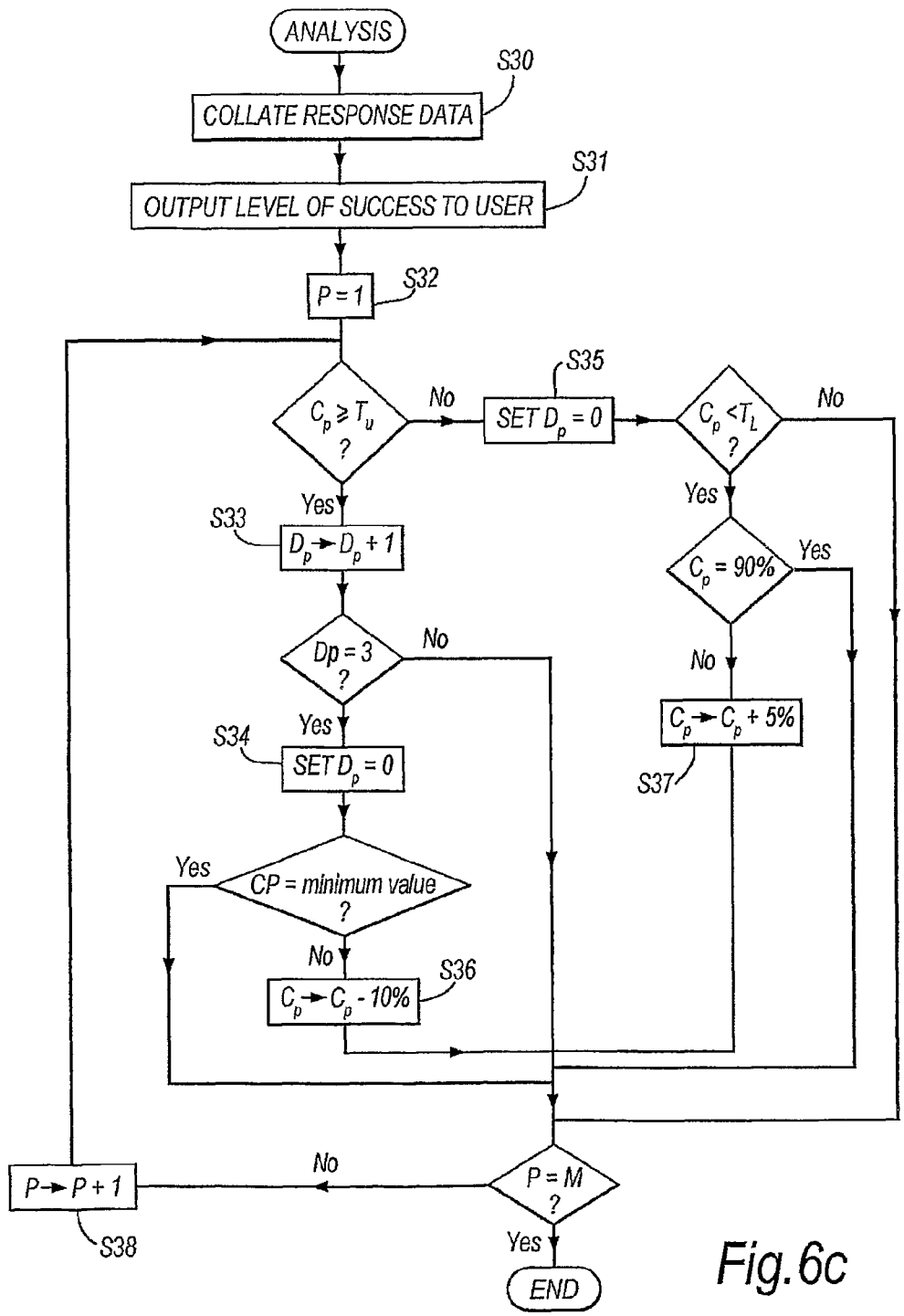

With reference to FIG. 6*c*, initially, the user's responses, which are stored in the database record for the user at S27, are collated by the system to determine the user's level of success, $S_P$, at detecting the visual stimulus for each of the predetermined locations (S30), and these results are output to the user (S31). For each display position P, if the level of success, $S_P$, is equal to or above an upper threshold value $T_U$, the value of the variable $D_P$ in the user's database record is incremented by 1 (S33), to indicate that the user may be considered to have reliably detected the visual stimulus during this session. It is then determined whether $D_P=3$, i.e., whether the user may be considered to have reliably detected the visual stimulus for three consecutive sessions. If $D_P=3$, the value of $D_P$ stored in the user's database record is reset to zero (S34), and the contrast setting $C_P$ is adjusted to correspond to a contrast value decreased by 10% (S36). However, if $D_P \neq 3$ the value of $D_P$ stored in the user's database record is not reset, and the contrast setting $C_P$ is not changed. Further, if the level of success, $S_P$, is below the upper threshold value $T_U$, the value of $D_P$ in the user's database record is reset to zero (S35).

In this way, the system is able to count the number of consecutive sessions for which the user may be considered to have reliably detected the visual stimulus for a particular display position.

It is then determined whether the level of success, $S_P$, is below a lower threshold value $T_L$. If this is the case, the contrast setting $C_P$ for that display position is adjusted to correspond to a contrast value increased by 5% (S37).

Thus, while three successful sessions will result in the contrast being lowered, if, on the performance following the contrast reduction, the performance falls to below the lower threshold, then the contrast is raised by 5%. Therefore, three significantly successful performances result in the task getting harder and one bad performance makes the task easier.

If the success rate $S_P$ lies between the threshold values, then the contrast setting $C_P$ for that display position is not changed. Similarly, if the contrast is set to maximum for a particular display position and the success rate for that position is less than $T_L$, or if the contrast is set to minimum and the success rate is equal to or above $T_U$ the value of the variable $C_P$ for that display position is not changed.

As indicated above, after the end of the second time interval, the system does not move on until the user has indicated their response. The user should thus be instructed to guess in which time interval the stimulus was displayed, if they have not been able to detect it.

Accordingly, even a user who is unable to detect any of the stimuli has a 50% chance of correctly identifying the time interval during which the stimulus was presented. It is, therefore, necessary to determine whether the success rate $S_P$ is greater than a success rate the user could have achieved by guessing. As N increases, the confidence level that a particular success rate is above what the user could have achieved by guessing also increases. Thus, a high value of N is desirable. However, increasing the value of N also increases the duration of the exercise. Since a user's ability to detect the visual stimuli begins to deteriorate due to tiredness after long periods using the apparatus, it is necessary to achieve a balance between the value of N and the duration of the exercise. In this respect, experiment has shown that users can cope with sessions of about 30 minutes per day. This allows for a value of N=50, if the process is to be repeated for 3 different display positions. With N=50 the confidence level for a success rate of 33/50 (66%) is p<0.05, while the confidence level for a success rate of 42/50 (84%) is p<0.001. On this basis it is considered that a user achieving a success rate of 42/50 or higher can be reliably determined to be able to detect the visual stimuli. Accordingly, where N=50, the upper threshold value $T_U$ for the success rate is set at 42/50=84%, and the lower threshold value $T_L$ is set at 33/50=66%. For different values of N, different threshold values must be determined. The CPU is configured to compute appropriate upper and lower threshold values, based on the value of N, using standard statistical techniques which would be straightforward for the person skilled in the art to implement. It will be appreciated that the values given above for the upper and lower thresholds for success rate, and for the confidence levels associated therewith, are merely examples taken from ranges of appropriate values.

The value of N and the duration of the exercise must also be balanced with the value of M. For a stimulus size whose diameter or side subtends an angle of 6 degrees, the number of different display positions required to activate the whole of the blind-field of the user could be a high number, depending on the size of the blind-field. However, for a value of N=50, this would mean the exercise lasting considerably longer than 30 minutes.

In some cases, exercises having a duration longer than 30 minutes may be appropriate. However, it is preferable that the coordinates of the display positions should be adjustable for different users, to target appropriate areas in the user's field of view. In this way, fewer than five display positions may be required. In this case, the coordinates of the display positions may be stored in the user's database record.

To assist the user to detect the visual stimulus, a fixation point in the form of a spot or cross-hatch is displayed on the screen, centred with respect to the display position of the visual stimulus. Unlike the visual stimulus itself, the fixation point appears on the screen throughout both time intervals in order to steady the gaze of the user in an appropriate direction.

In circumstances where a user is consistently unable to detect the visual stimulus, this may have a detrimental affect on the morale of the user. One measure to avoid this, and to maintain the user's interest, is for the visual stimulus to be presented, at random intervals throughout the exercise, at a location corresponding to or at least partially overlapping an area of the user's field of view where they are easily able to detect the stimulus. The user response for stimuli presented at such locations should be discounted when collating the response data, as they do not have any bearing on the user's ability to detect the stimulus in the display area being exercised. As a further measure, an audio signal can inform the patient if they have correctly identified the time interval during which the stimulus was presented.

For best results, a user should undertake one session per day for at least 90, preferably consecutive, days. However, positive results may also be obtained if one or two days per week are missed.

In this respect, a significant advantage of the present invention is its versatility, which means that it is suited to being installed in a user's home environment as well as in laboratory or clinical settings, and that it is straightforward for a user to use without the supervision of an operator. This means that the user does not need to travel to a hospital or clinic every day to use the apparatus.

While the embodiment of the invention described above uses a method where a visual stimulus is displayed to the user during one of two time intervals, and the user indicates in which of the two intervals they believe the visual stimulus was displayed, other methods are also possible. For example, a method where the visual stimulus is presented during a single time interval with its start and end marked by audio signals, and the user indicates whether or not they saw anything.

Although, in the present embodiment, the contrast of the stimuli are adjusted based on the performance of the user after three consecutive sessions, in alternative embodiments, the system may be configured such that the user's performance over any number of sessions is evaluated before the contrast of the stimuli are adjusted.

Figure 7C:
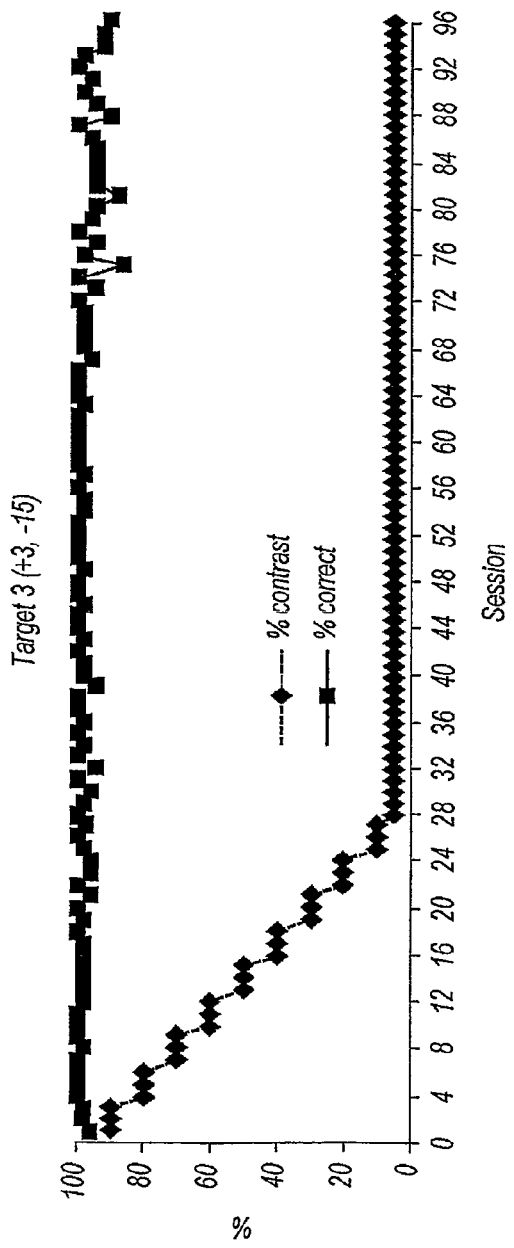

If used effectively the apparatus of the present invention can significantly improve the sensitivity within the blind-field of users having cortical blindness caused by brain damage. Response data for a user who used the apparatus over 96 sessions is illustrated in FIGS. 7a to 7c. Each graph represents data for a particular display position, or "target" of the user's field of view, and illustrate percentage contrast (♦) and success rate (■) on the y-axis, plotted against session number on the x-axis. The contrast data, indicated by the symbol ♦, represents the contrast setting of the visual stimuli presented to the user for each session, and the success rate data, indicated by the symbol ■, represents the success rate of the user at detecting the visual stimulus during that session.

As may be seen from FIG. 7c, the user achieved a near perfect success rate for the display position "target 3", indicating that this display position Corresponded to a sighted region of their field of view. Consequently, the contrast setting of the stimulus, which is initially set at 90%, is reduced by 10% every three sessions, and finally by 5% after the $27^{th}$ session, where it reaches the minimum contrast of 5%, and remains at this minimum contrast setting for the remaining sessions.

In contrast, the graphs in FIGS. 7a and 7b show a success rate of about 50% for the initial 25-30 sessions. This success rate is consistent with what the user could be expected to achieve by guessing, indicating that the user was unable to detect the stimulus at these two display positions at all during these initial sessions. However, after the initial sessions, the success rate can be seen to gradually increase as the user's ability to detect the stimulus improves. When the user achieves a success rate above a threshold value of about 80% for three consecutive sessions, the contrast of the stimulus is reduced by 10%. Over time this results in an improvement in the user's sensitivity to the stimulus so that they are able to detect the stimulus with reduced contrast. At the end of the sessions, the patient can detect much lower contrast targets and becomes aware of these events in their blind-field hence increasing their sensitivity.

EXPERIMENTAL EXAMPLE

Overview

A group of 15 patients suffering from visual field defects undertook a daily training program for a period of 3 months using a vision exercising apparatus and method according to the present invention. A range of subjective and objective measures of visual sensitivity before and after the training sessions have shown evidence for increased visual sensitivity.

Procedure

Patients visual fields were assessed in two separate sessions using a Humphrey Automated Perimetry (10-2 and 30-2 full threshold) before the training program. Based on visual field data, in each case two separate field locations were identified, one as a candidate for repeated stimulation during the training, and a second as a control area which was not stimulated. During 4-6 separate visits to the laboratory, a number of measurements were carried out prior to the training to obtain baseline measurements of visual sensitivity for each individual. These included detection of a range of spatial frequencies, contrast detection at 1 cycle/°, and visual fields measurements using automated perimetry as well as subjective fields. These were repeated 3 months later to ascertain the effect of repeated stimulation in the intervening period.

The training program itself consisted of 50 trials at 3 different visual field locations (150 trials in total), being the visual field location where baseline measurements were carried out, along with two other adjacent locations, one further into the field defect and a second often straddling the borders of absolute blindness as identified by perimetry. Presentations on the blind field borders were included to keep the patient's attention on the task and to avoid boredom due to monotonous presentation of stimuli within the blind area.

Each trial involved patients discriminating a vertical sinusoidal grating versus a uniform field in a temporal two-alternative forced-choice task. The gratings used were circular patches (1 cycle/° modulated temporally at 10 Hz, with space averaged luminance the same as the background (37 cd/m2). Initially, all grating contrasts were set to 90% (Michelson contrast) and the contrasts for stimuli in all locations were kept constant during each session. The grating contrasts were then changed at the end of each session to keep the performance consistent.

The two temporal intervals in each trial were signalled with audio beeps and a separate audio beep signalled the end of the trial. Patients indicated in which of the two intervals the grating was presented via a response box. This provided so-called "discrimination data".

In addition, using a commentary-key-paradigm, after each trial patients also reported if they had any awareness of the stimulus presentation on a binary scale via the response box. Patients were asked to respond "no" only if they had no awareness whatsoever of the visual stimulus. This provided so-called "reported awareness data".

No feedback was given to the patients as to whether they were correct after each trial nor was it given after each session, therefore, the patients were totally unaware of their performance scores throughout the training program.

Results

Of the group of 15 patients recruited for the purpose of this study, 3 patients were excluded, 2 for withdrawing from the study prior to completion and 1 who had a second stroke shortly before commencing post training tests.

Detection of High Contrast Gratings at Various Spatial Frequencies

Figure 8A:
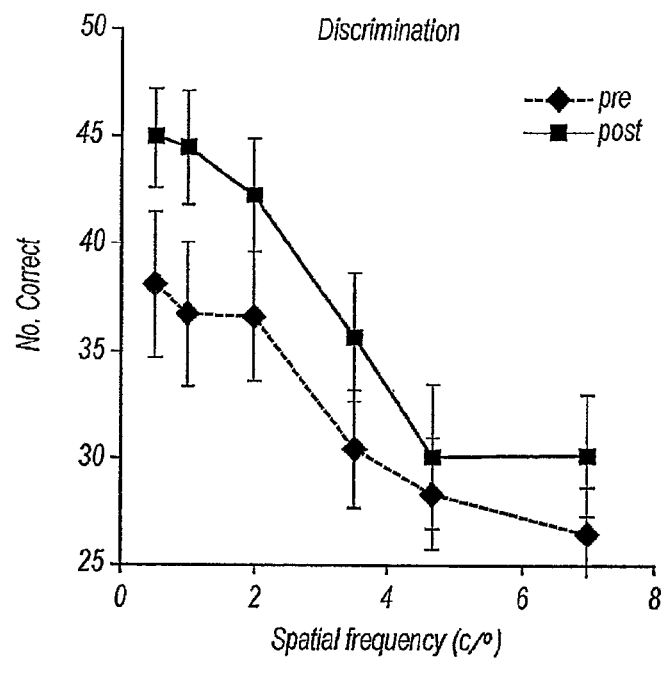
FIGS. 8a and 8b are graphs showing the results of an experimental example of the detection of high contrast gratings at various spatial frequencies in group of patients before and after completion of a training program.
Figure 8B:
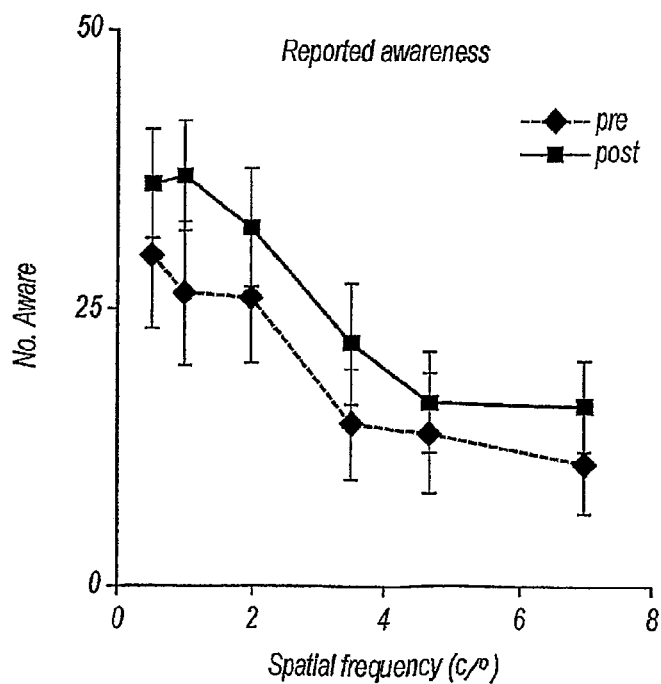

Prior to the start of the training program, patients reported the interval in which a temporally modulated (10 Hz) Gabor patch, limited to $\pm 2\sigma_z$ where the standard deviation of the spatial envelop ($\sigma_z$)=2.5°, standard deviation of the temporal Gaussian envelope ($\sigma_t$)=500 ms; duration 2s ($4\sigma_t$) with carrier frequencies in the range of 0.5-7 cycles/° was presented. The stimulus contrast was fixed at 50% for all patients. The remaining interval contained a uniform field with luminance equivalent to the space-averaged luminance of the Gabor patch (37 cd/m$^2$). The results are shown in FIGS. 8a and 8b, with results before the (pre) training program marked with diamonds (♦) and results after the (post)training program marked with squares (■). With regard to discrimination data, paired-sample comparisons showed significant improvement post-training for spatial frequencies of 0.5 cycles/° (t=3.179, df=6, p<0.01) and 1 cycles/° (t=2.376, df=6, p<0.027), 2 cycles/° (t=2.716, df=6, p<0.017) and 3.5 cycles/° (t=3.113, df=6, p<0.011). The improved performance did not reach significance at 4.7 and 7 cycles/°.

With regard to reported awareness data, paired sample comparisons revealed significant improvement post-training for spatial frequencies of 0.5 c/° (t=2.120, df=6, p=0.039) and 1 cycles/° (t=2.556, df=6, p<0.022), but not significant at 2 cycles/° (t=1.408, df=6, p<0.11) and 3.5 cycles/° (t=1.445, f=6, p<0.2) and lower frequencies.

Figure 9A:
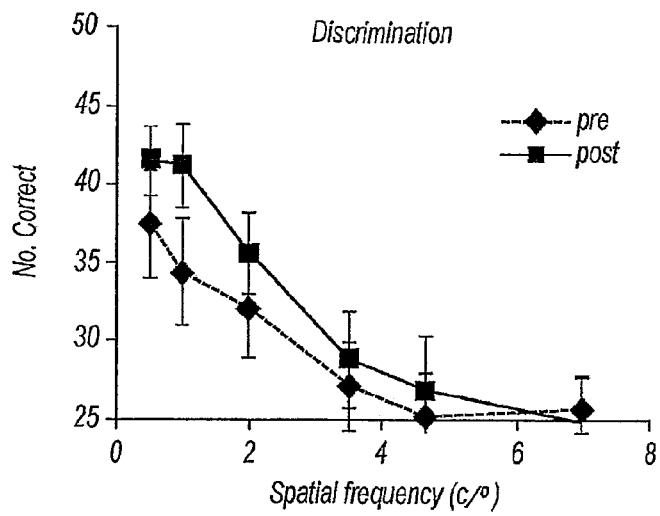
FIGS. 9a and 9b are graphs showing the results of an experimental example of the detection of high contrast gratings at various spatial frequencies for stimuli presented to a control location before and after the training program.
Figure 9B:
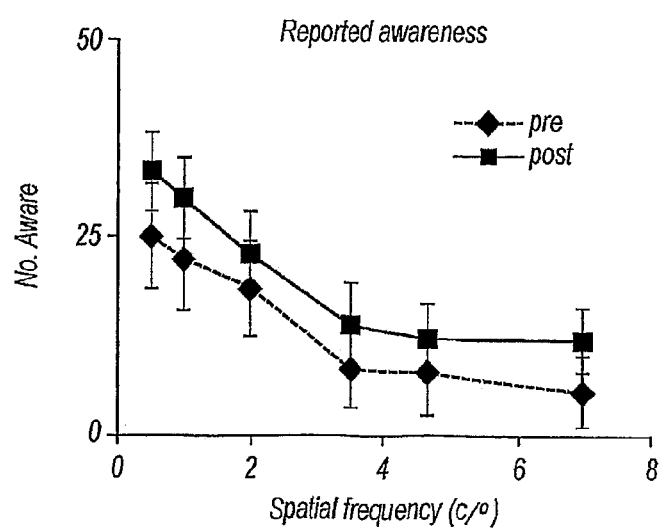

FIGS. 9a and 9b show the discrimination and awareness reports of the group of patients for stimuli presented to a control location before and after the training program. All the stimulus parameters were the same as above, reported for the training area, except that none of the patients received systematic stimulation in the control area during training to investigate whether any improvements were specific to the training task. The results indicate that in control area, following training, there is no significant improvement in reported awareness at any of the spatial frequencies tested.

The improvements in discrimination, although statistically significant, covers a narrower range of spatial frequencies than those for the training area.

Detection of a 1 Cycle/° Gabor Patch at a Range of Contrasts

Figure 10A:
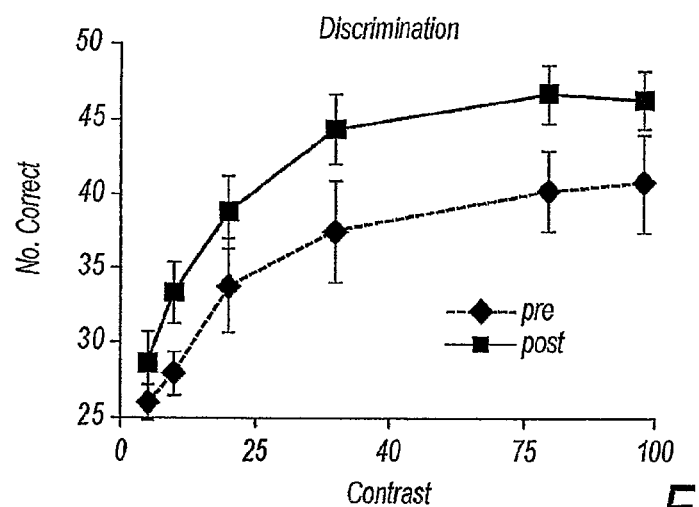
FIGS. 10a and 10b are graphs showing the results of an experimental example of the detection of a 1 cycle/° Gabor patch at a range of contrasts in group of patients before and after completion of the training program.
Figure 10B:
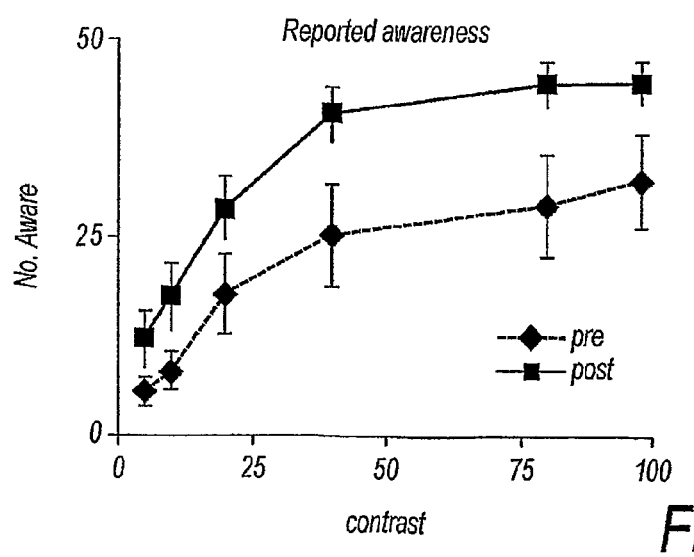

The peak sensitivity of the residual spatial channel and the repeated stimulation were set at 1 cycler with temporal modulation set at 10 Hz, the detection of the same stimulus in the training area at a range of contrast levels (5%, 10%, 20%, 40%, 80%, 98%) was measured before and after the training exercise. The results are shown in FIGS. 10a and 10b, with results before the (pre) training program marked with diamonds (♦) and results after the (post)training program marked with squares (■).

With regard to discrimination data, paired-sample comparisons showed significant improvement post-training for all contrasts except for the lowest (5%).

With regard to reported awareness data, post-hoc paired-sample comparisons showed that significant improvement post training for all contrasts except for the lowest (5%).

Assessment of Visual Field Sensitivity

Figure 11:
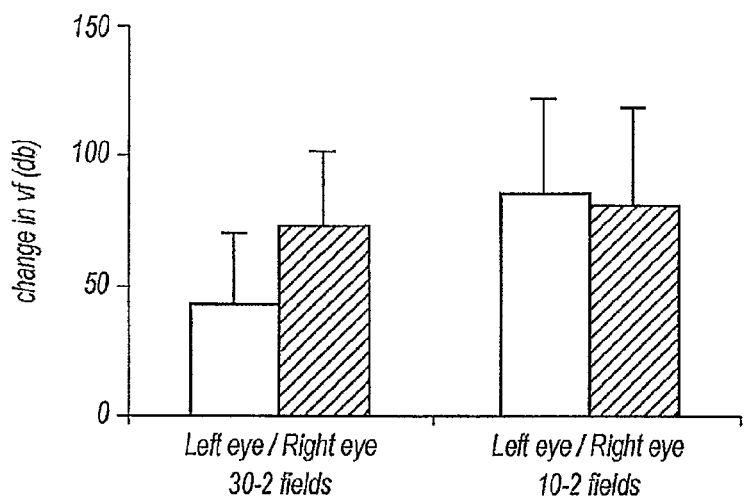
FIG. 11 shows the results of an experimental example of the change in the visual field sensitivity in central 10 and 30 degrees in group of patients after completion of the training program.

As discussed above, visual field sensitivity in central 10 and 30 degrees in all patients was assessed using a Humphrey Automated Visual Field Analyser (VFA) before and after completion of the training program. For each patient, the change in sensitivity following training was determined by summing the decibel change (db) in the affected hemifield for each eye and then averaging the data of both eyes. The results are shown in FIG. 11.

Both central 10 and 30 degrees showed increased sensitivity. The increased visual field sensitivities were significant (one-sample t-test against value 0) for both central 10 (t=2.062, df=10, p=0.033) and 30 degrees (t=1.852, df=11, p<0.046). There were no significant differences in improvements between the eyes for the central 10 degrees (t=0.853, p=0.413, 2-tailed), but the right eye appeared more sensitive than the left over the central 30 degrees (t=2.684, df=11, t=0.021, 2-tailed).

Figure 12:
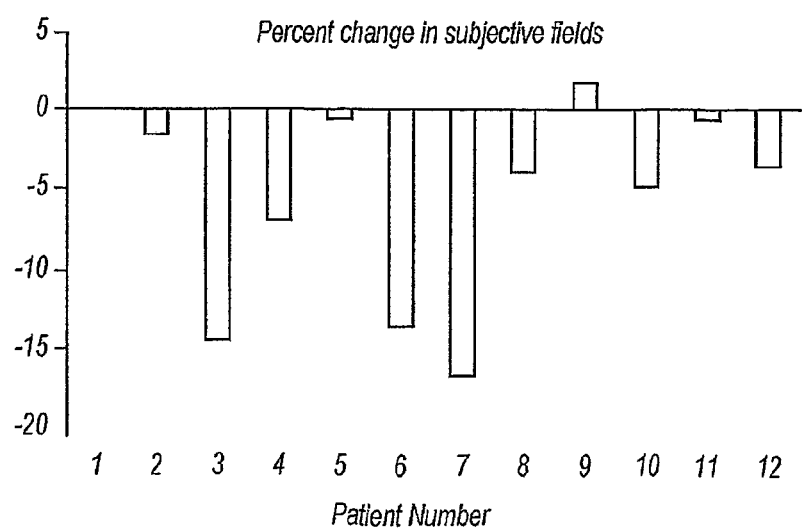
FIG. 12 shows the results of an experimental example of the change in subjective perception of a group of patients' visual field defects after completion of the training program.

In addition, each patient's own subjective perception of their field defect was estimated by asking each patient to draw within a circle, their perception of their field defect. By calculating the change in affected area, before and after the training, inferences can be made about any perceived change. The results are shown in FIG. 12. The subjective visual field loss averaged between left and right eye, indicated a significant shrinkage of the field defect (t=3.096, df=10, p=0.011, 2-tailed). The apparent shrinkage of the field defect following the training appeared to be similar in the two eyes (t=2.110, df=10, p=0.061).

The results of the testing demonstrated that repeated stimulation with optimal stimuli can result in increased performance in the detection tasks. By changing the contrast of stimuli, the task difficulty was kept consistent during the training, and patients were able to detect gratings at lower contrast levels at the end of three months of training, compared to the beginning of the training task.

It is believed that the success of the approach outlined in the present application in improving sensitivity in a blind field region is due to the brain perceptually learning to interpret signals from surviving neurons neighbouring those which have been damaged in the visual cortex.

In this connection, there are numerous cortical and sub-cortical structures within the visual cortex that are involved in interpreting visual stimuli, forming a multitude of candidate routes mediating blindsight performance. As such, the neighbouring neurons which survive an initial injury causing cortical blindness provide residual visual capacities known as "blind sight". By repeatedly stimulating the blind field region using optimum spatial and temporal properties, the present invention allows the brain circuitry to learn to make use of these alternative processing routes. Effectively, it is believed that, over time the brain learns to recognise and interpret the "blind sight" stimulations, leading to improved sensitivity, even deep within the visual field defect.

In contrast to the stimulus provided by the present invention, everyday (environmental) visual stimulations do not lead to improvements in visual sensitivity of visual field defect of a person with cortical blindness. This is because the stimulation provided by the present invention is optimised for the pathways mediating blind sight. Furthermore, people with cortical visual field defects learn to ignore their area of blind field and pay more attention to their areas of normal vision in everyday interactions. With the present invention, however, a persons is encouraged to focus on stimulation from their area of blind field. This also contrasts with conventional rehabilitation methods which merely focus on stimulating the outer boundary region of a visual field defect.

The invention claimed is:

1. Vision exercising apparatus comprising:
   a visual display device;
   locating means for locating the head of a user at a position to provide a substantially known relationship between the visual display device and the field of view of the user;
   display position control means for actuating the visual display device to display a temporally modulated visual stimulus at a known display position, the display position corresponding to a specific viewing area of the field of view of the user whilst located in the locating means;
   user actuable response means actuable by the user to enable a user response to be provided when the user considers the temporally modulated visual stimulus has been viewed during use of the apparatus;
   further control means to control the display position control means to repeatedly display the temporally modulated visual stimulus at the known display position; and
   means to collate, for the present user, user response to display of the temporally modulated visual stimulus at the known display position and to evaluate the statistical significance of the user response for that display position;
   wherein the visual stimulus is temporally modulated by flashing or counterphasing the visual stimulus at a predetermined temporal frequency;
   wherein the visual stimulus comprises alternating dark and light features contained within a boundary that subtends an angle substantially in the range from 2 to 12 degrees in the field of view of the user; and
   wherein the further control means controls the display position control means to reduce the contrast of the temporally modulated visual stimulus when the statistical significance of the user response is greater than a predetermined level and increases the contrast of the temporally modulated visual stimulus when the statistical significance of the user response is less than a predetermined level.

2. Apparatus as claimed in claim 1 wherein the further control means controls the display position control means to display at a particular display position according to the current user.

3. Apparatus as claimed in claim 1 wherein the further control means controls the display position control means to display the temporally modulated visual stimulus at a known display position a particular number of times during a single usage of the apparatus.

4. Apparatus as claimed in claim 1 wherein the further control means controls the display position control means to display the temporally modulated visual stimulus at a particular number of known display positions during a single usage of the apparatus.

5. Apparatus as claimed in claim 1 wherein the further control means controls the display position control means to display the temporally modulated visual stimulus at a maximum contrast for a new user of the apparatus.

6. Apparatus as claimed in claim 1 wherein the further control means controls the display position control means to reduce the contrast of the temporally modulated visual stimulus by a greater amount than the amount by which the display control means increases the contrast.

7. Apparatus as claimed in claim 1 wherein the further control means controls the display position control means to reduce the contrast of the temporally modulated visual stimulus by an amount equal to the amount by which the display control means increases the contrast.

8. Apparatus as claimed in claim 1 further comprising means for providing the user with an indication of when display of the temporally modulated visual stimulus could take place.

9. Apparatus as claimed in claim 8 wherein said means for providing the user with an indication of when display of the temporally modulated visual stimulus could take place comprises an audible signal and means for presenting said audio signal to the user in predetermined timing relationship to the display.

10. Apparatus as claimed in claim 1 wherein said temporally modulated visual stimulus is in the form of a grating comprising a plurality of cycles of alternating dark and light linear features.

11. Apparatus as claimed in claim 10 wherein the number of cycles of alternating dark and light linear features is substantially in the range 0.01 to 10.0 per angular degree of the field of view.

12. Apparatus as claimed in claim 11 wherein the number of cycles of alternating dark and light linear features is substantially in the range 0.5 to 7.0 per angular degree of the field of view.

13. Apparatus as claimed in claim 12 wherein the number of cycles of alternating dark and light linear features is substantially 1.0 per angular degree within the field of view.

14. Apparatus as claimed in claim 1 wherein the temporally modulated visual stimulus is in the form of dots and/or checks.

15. Apparatus as claimed in claim 1 wherein the boundary comprises a substantially circular boundary.

16. Apparatus as claimed in claim 1 wherein the boundary comprises a substantially square boundary.

17. Apparatus as claimed in claim 15 wherein the diameter of the substantially circular boundary subtends an angle of substantially 6 degrees in the field of view of the user.

18. Apparatus as claimed in claim 1 wherein the further control means controls the display position control means to display the temporally modulated visual stimulus at a temporal frequency substantially in the range of 1 to 30 Hz.

19. Apparatus as claimed in claim 18 wherein the further control means controls the display position control means to display the temporally modulated visual stimulus at a frequency of substantially 10 Hz.

20. Apparatus as claimed in claim 1 further including attraction means to attract the gaze of the user to a preselected position to assist in providing the substantially known relationship between the visual display device and the field of view of the user.

21. Apparatus as claimed in claim 1 wherein said user actuable response means comprises a tactile electronic device whose condition can be changed by touch or motion in response to the observer's perception of said stimulus.

22. Apparatus as claimed in claim 1 wherein the use actuable response means is voice operated.

23. Apparatus as claimed in claim 1 wherein the visual display device comprises a computer screen or projector.

24. Apparatus as claimed in claim 1 wherein the locating means comprises an adjustable chin rest.

25. Apparatus as claimed in claim 1 further comprising memory means for storing one or more user profiles and wherein deficient areas in the user field of view are stored in the memory means;

wherein the further control means selects the known display position according to the profile and stores in the memory means the user response to display of the temporally modulated visual stimulus at the known display position.

26. Apparatus as claimed in claim 25 wherein the further control means selects the known display position to correspond to a viewing area of the field of view of the user where the user has restricted or no vision.

* * * * *